United States Patent [19]

Heinonen et al.

[11] Patent Number: 6,096,752

[45] Date of Patent: Aug. 1, 2000

[54] METHOD FOR THE PREPARATION OF TERTIARY AMINES, A COMPOUND USEFUL THEREFOR AND ALPHA-2-RECEPTOR ACTIVE TETRAHYDROISOQUINOLINE DERIVATIVES

[76] Inventors: Petri Heinonen, Ursininkatu 7 b A 15, FIN-20100 Turku; Harri Lönnberg, Vatjankatu 3, FIN-20750 Turku; Victor Cockcroft, Yliopistonkatu 5 A 9, FIN-20101 Turku, all of Finland

[21] Appl. No.: 09/167,740

[22] Filed: Oct. 7, 1998

Related U.S. Application Data

[62] Division of application No. 08/909,823, Aug. 12, 1997, Pat. No. 5,912,342.

[51] Int. Cl.$^7$ .................................................. C07D 217/00
[52] U.S. Cl. ............................................................ 514/260
[58] Field of Search ............................................... 546/139

[56] References Cited

U.S. PATENT DOCUMENTS 3,988,339 10/1976 Kaiser et al. ............................ 546/139

FOREIGN PATENT DOCUMENTS

Wo 95/34326 12/1995 WIPO .

*Primary Examiner*—Zinna Northington Davis
*Attorney, Agent, or Firm*—Kubovcik & Kubovcik

[57] ABSTRACT

The invention relates to the preparation of teriatry amines of the formula (V)

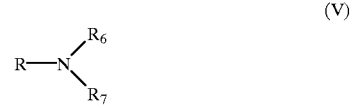

(V)

where R is alkyl and $R^6$ and $R^7$ are alkyl groups which are optionally substituted or where $R^6$ and $R^7$ form a ring or ring system, via a substrate which is a compound of the formula (I)

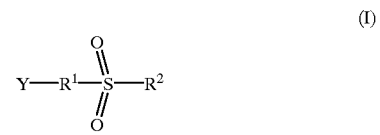

(I)

wherein
Y is the fraction of a solid or soluble support, where Y may include a residue of a functional group having been attached to said support, said functional group having been hydroxy, amino, thio, epoxy or halogen,
$R^1$ is aryl, heteroaryl, alkyl chain or a ring or ring system, which may include a heteroatom, or $R^1$ is nothing, and $R^2$ is vinyl; $CH_2CH_2X$, where X is halogen; or $R^3C{=}CHR^4$ or $R^3CH{-}CH_2R^4X$, where $R^3$ and $R^4$ are the same or different and are alkyl, acyl, carbonyl, cyano or nitro groups and X is halogen. The invention particularly relates to the preparation of alpha-2-receptor active tetrahydroisoquinoline derivatives.

7 Claims, No Drawings

METHOD FOR THE PREPARATION OF TERTIARY AMINES, A COMPOUND USEFUL THEREFOR AND ALPHA-2-RECEPTOR ACTIVE TETRAHYDROISOQUINOLINE DERIVATIVES

This application is a division of application Ser. No. 08/909,823, filed Aug. 12, 1997 now U.S. Pat. No. 5,912,342.

FIELD OF THE INVENTION

This invention relates to a method for the preparation of tertiary amines, a compound useful therefor, and to alpha-2-receptor active tetrahydroisoquinoline derivatives.

BACKGROUND OF THE INVENTION

The publications and other materials used herein to illuminate the background of the invention, and in particular, cases to provide additional details respecting the practice, are incorporated by reference.

The art of synthesising combinatorial libraries has become a routine technique transferable to be done by computer controlled robots allowing large numbers of compounds to be prepared rapidly (1). On the other hand, the trend, which can be seen in combinatorial chemistry, is from synthesis of large oligomeric compounds (e.g. peptides, peptoids or oligonucleotides) produced and tested in a form of complex mixtures, to libraries containing relatively small organic molecules, which are made in a parallel mode. Most of the library syntheses are made on a solid support using resins and linkers originally developed for peptide or oligonucleotide chemistry (2). Because wide structural diversity of compounds in small molecular libraries is needed, it is obvious that existing linkers for solid phase chemistry have severe limitations.

OBJECT AND SUMMARY OF THE INVENTION

The object of the present invention is to provide a novel compound useful as a substrate in the synthesis of tertiary mines, methods for the preparation of said compound, the use of said compound in the synthesis of tertiary amines, and novel alpha-2-receptor active 1,2,3,4-tetrahydroisoquinolines.

The object of the present invention is to provide a compound which has the following advantages over known linkers (3, 4): i) it has no ester or amide functionality susceptible to hydrolysis during library synthesis, ii) it allows fast quaternization of the bound secondary amine, and iii) the cleavage of the tertiary amine from the compound is easy and rapid.

Thus, according to one aspect of the invention, a novel compound of the formula (I) is provided

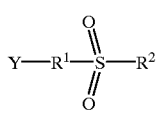
(I)

wherein

Y is the fraction of a solid or soluble support, where Y may include a residue of a functional group having been attached to said support, said functional group having been hydroxy, amino, thio, epoxy or halogen, $R^1$ is aryl, heteroaryl, alkyl chain or ring or ring system, which may include a heteroatom, or $R^1$ is nothing, and $R^2$ is vinyl;

$CH_2CH_2X$, where X is halogen; or $R^3C=CHR^4$ or $R^3CH—CH_2R^4X$, where $R^3$ and $R^4$ are the same or different and are alkyl, acyl, carbonyl, cyano or nitro groups and X is halogen.

The advantages of compound (I) are due to the stability of the linkage connecting the sulfur atom to the solid or soluble support, and the strongly electron withdrawing properties of the sulfone moiety.

According to another aspect the invention concerns a method for the synthesis of a compound according to the formula (I) as defined above

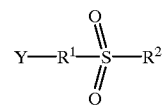
(I)

wherein a compound Supp-Z, where Supp is a solid or soluble support optionally having a tethering group such as methylene for linking a functional group Z to said support, and Z is hydroxy, amino, thio, epoxy, halogen or alkylsulfonyloxy, is reacted in the presence of a base with a compound of the formula

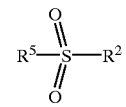

wherein $R^2$ is the same as defined above and $R^5$ is vinyl, $XR^1$ or $HR^1$, where X is halogen and $R^1$ is the same as defined above, provided that when Z is halogen, then $R^5$ must be $HR^1$.

According to a third aspect, the invention concerns the use of a compound according to formula (I) as defined above, as a substrate in the synthesis of a tertiary amine from a secondary amine wherein said secondary amine optionally is derivatized while being attached to said substrate.

According to a fourth aspect, the invention concerns a method for the synthesis, using as a substrate a compound of formula (I) as defined above, of a tertiary amine (V)

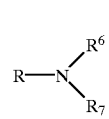
(V)

where R is alkyl and $R^6$ and $R^7$ are alkyl groups which optionally are substituted or where $R^6$ and $R^7$ form a ring or ring system, wherein said method comprises the steps of
a) reacting the compound (I)

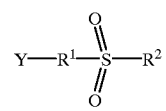
(I)

wherein Y, $R^1$ and $R^2$ are the same as defined above, with a secondary amine (II)

(II)

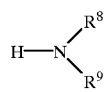

wherein $R^8$ and $R^9$ are the same as or different from the groups $R^6$ and $R^7$ groups defined above and are alkyl groups or form a ring or ring system, to give a compound (III)

(III)

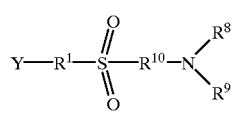

wherein $R^{10}$ is $CH_2CH_2$ or $R^3CH\!-\!CHR^4$, where $R^3$ and $R^4$ are the same as defined above, b) quaterizing the compound (III) with an alkyl halide RX where R is alkyl and X is halide or an ester of an alkyl sulfonic acid, to give a quaternary ammonium ion (IV)

(IV)

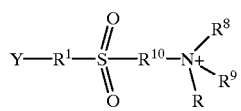

c) cleaving the quaternary ammonium ion (IV) to give a tertiary amine (V), and, in case $R^8$ and $R^9$ are different from $R^6$ and $R^7$, carrying out the reactions interchanging these groups as separate steps between steps a) and b) above.

According to a fifth aspect, the invention concerns an alpha-2-receptor active compound of the formula (VI)

(VI)

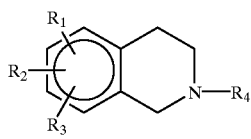

wherein $R_1$, $R_2$, and $R_3$, which can be the same or different and which are H, alkyl or an ether group $O\!-\!(CH_2)_n R_5$, wherein $(CH_2)_n$ is straigth or branched and n is an integer from 1 to 14 and $R_5$ is H, alkyl, aryl, a ring or ring system and wherein $(CH_2)_n R_5$ may be unsubstituted or substituted with one or more substituent being OH; CN; $NO_2$; carbonyl; halogen; $SSO_2Me$ (where Me is methyl); phthalimido; $NR_6R_7$, where $R_6$ and $R_7$ are alkyl groups; an aromatic ring or ring system; a heterocyclic ring or ring system, particularly 1,3-dioxane or indole; an ether group such as phenoxy or benzyloxy, wherein the benzene ring may be substituted or unsubstituted;

$R_4$ is H, or a lower alkyl, which may be unsubstituted or substituted, the substituent being particularly an alkoxy or hydroxyalkoxy group;

provided that $R_1$, $R_2$ and $R_3$ cannot all simultaneously be hydrogen;

and a pharmaceutically acceptable salt thereof.

DETAILED DESCRIPTION OF THE INVENTION

The term "Solid support" means a material insoluble in commonly used organic solvents, which can be used to bind covalently chemical compounds. These include materials such as porous glass, silica, and organic polymers such as polystyrene, which can be crosslinked with divinylbenzene, or which can be grafted with polyethylene glycol. These materials have one or more functional groups, which can be used to react with various types of organic molecules to form covalent linkage.

As examples of solid support forming Y in formula (I) can be mentioned:

polystyrene-based:
    hydroxymethylene polystyrene
    aminomethylene polystyrene
    thiomethylene polystyrene
    chloromethylene polystyrene polyethylene glycol-grafted polystyrene:
    TentaGel™ OH
    ArgoGel™ OH
    TentaGel™ NH
    ArgoGel™ NH
    ArgoGel™ Cl controlled pore glass (CPG):
    long chain aminoalkyl CPG agarose or sepharose:
    epoxy-activated agarose matrix The term "Soluble support" means a polymer or non-polymer support, which is soluble in solvents used during reaction steps forming, in the case of matter, tertiary amine, but which can be precipitated using other organic solvents, such as acetone. As examples of such soluble supports can be mentioned: polyethylene glycol, polystyrene, polyvinylene and the like.

For many polymers, the length of the polymer chain determines whether the polymer is solid or soluble.

According to a preferred embodiment, $R^1$ in compound (I) is $CH_2CH_2$ or nothing.

A preferred group of compounds of formula (I) is the compounds

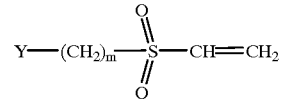

wherein m is 0 or 2 and Y has the formula Supp-O or Supp-NH and Supp is the support optionally including a tethering group such as methylene, to which the functional hydroxy or amino group has been attached.

Methods for the synthesis of compounds of formula (I) are listed in Scheme I. In Scheme I $R^1$, X and Y have the same meaning as in the definition of the compound of formula (I) and Y' means the solid or soluble support without functional group or residue thereof.

As specific examples of compounds of formula (I) can be mentioned compound 1a (Scheme IIa) and compound 1b (Scheme IIb).

The compound 1a (Scheme IIa) may be prepared by catalytically adding divinyl sulfone to hydroxymethylated polystyrene beads in the presence of an organic base, for example DBU (1,8-diazabicyclo-[5.4.0]undec-7-ene) or the like. The compound 1b (Scheme IIb) may be prepared by adding vinylsulfonyl chloride to aminomethylated polystyrene beads, also in the presence of an organic base such as DBU.
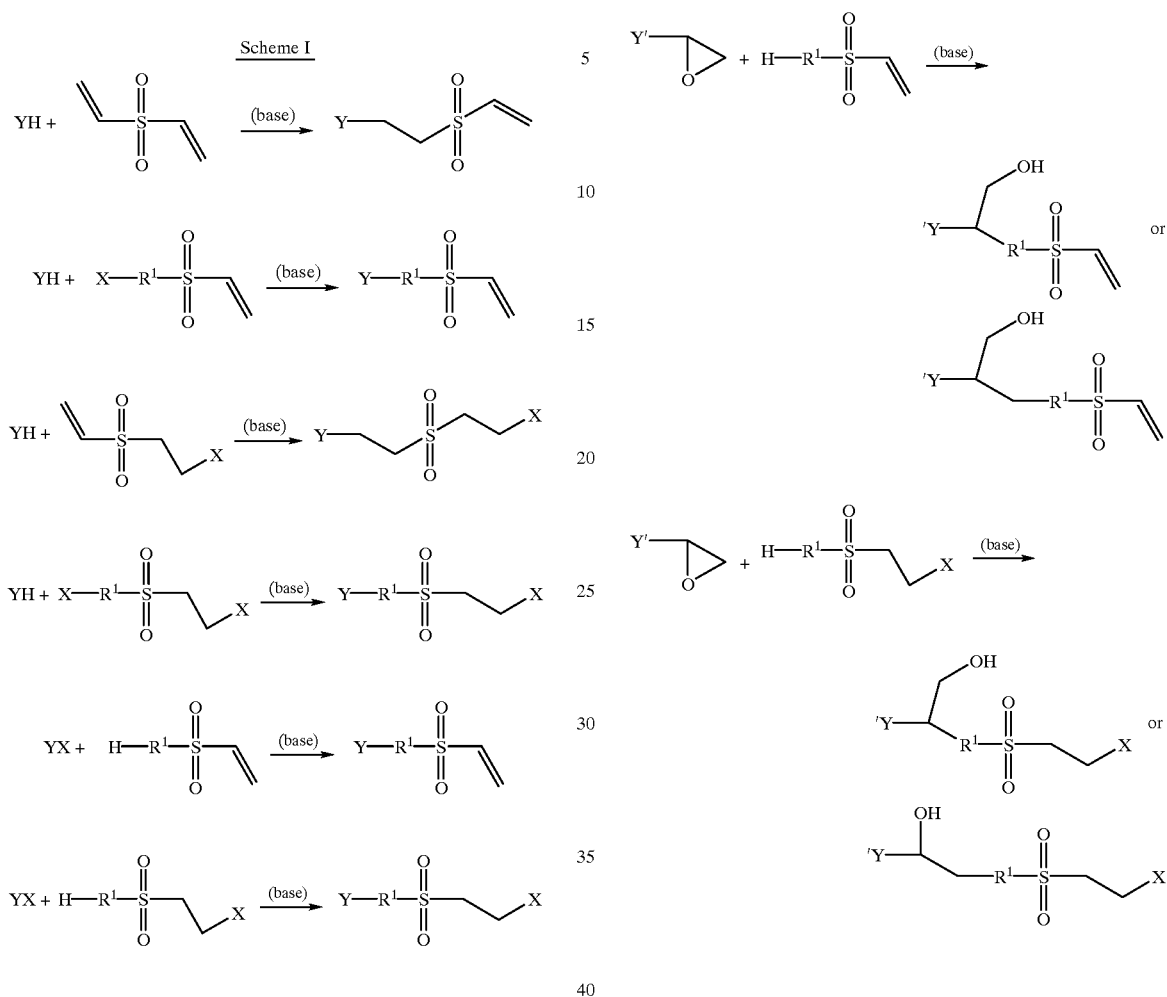
Scheme IIa
Synthesis of compound 1a and its use in the synthesis of N-alkylated tetrahydroisquinolines (PS = polystyrene, $R_1$, $R_2$, $R_3$ = alkoxy or H; $R_4$ = alkyl, X = Cl, Br, I or $RSO_2O$)
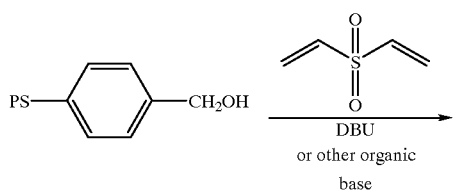

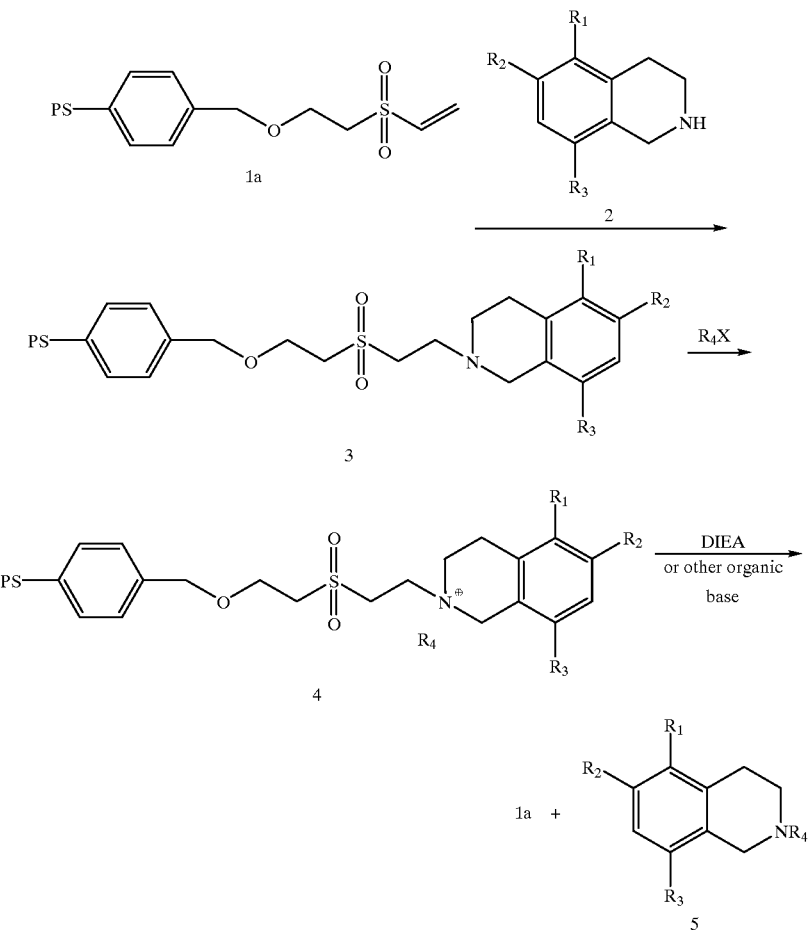
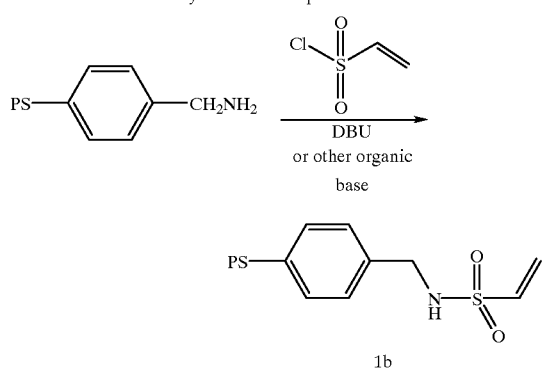
Scheme IIb
Synthesis of compound 1b
Scheme III
Diversity generation in the aromatic ring of tetrahydroisoquinoline by solid phse Mitsunobu reaction after deprotection of phenolic hydroxy function
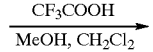
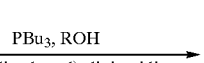

-continued

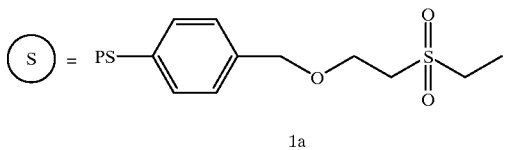

1a

Compound (I) of this invention is useful for the synthesis of any tertiary amine

(V)

where R is alkyl and $R^6$ and $R^7$ are alkyl groups which optionally are substituted or where $R^6$ and $R^7$ form a ring or ring system. The wording "ring or ring system" used in this formula and in this text generally shall be understood to include aliphatic, aromatic and heterocyclic rings, and the "ring system" means a combination of at least two rings, said rings being attached to each other so that they have at least one common atom.

The alpha-2-receptor active compound of the formula (VI) has preferably the substituents in the following position: $R_1$ in the 5-position, $R_2$ in the 6-position and $R_3$ in the 8-position of the tetrahydroisoquinoline ring system. The formula of this subgeneric group is:

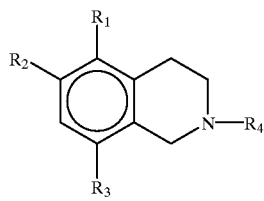

According to a preferred embodiment, two of the substituents $R_1$, $R_2$ and $R_3$ are hydrogen and the third one is an ether group $O-(CH_2)_nR_5$.

EXPERIMENTAL

General Methods

Chromathographic purifications were carried on Kieselgel 60 (Merck) silica gel, and TLC analyse on Alufolien Kieselgel 60 $F_{254}$ (Merck) TLC plates, using the following eluent systems: System A: dichloromethane, B: methanol:dichloromethane 1:99 (v/v), C: methanol:dichloromethane 3:97 (v/v, D: methanol:dichloromethane 7:93 (v/v), E: methanol:dichloromethane 1:9 (v/v). The NMR spectra were recorded on JEOL JNM-GX 400 or JEOL JNM-A 500 NMR spectrometers. The chemical shifts are given in ppm from internal tetramethylsilane. The mass spectra were recorded on a 7070E VG mass spectrometer.

HPLC Analysis

HPLC analysis were carried out on Merck-Hitachi instrument consisted of L-7100 Gradient Pump, L-7400 UV detector, and D-7500 Chromato-Integrator. The crude products from cleavage were analysed by reversed phase chromathography. (Column: LiChroCART 125-3, containing Purospher RP-18e sorbent; eluent: Acetonitrile:buffer 10:90; buffer: 0.050 mol $L^{-1}$ $KH_2PO_4$, pH 2.00; flow rate: 0.75 mL $min^{-1}$; detection: 276 nm).

The use of compound (I) is demonstrated in the following in the synthesis of a special group of tertiary amines, namely N-substituted 1,2,3,4-tetrahydroisoquinolines. These compounds are of importance because of their alpha-2-receptor activity. Scheme IIa demonstrates the synthesis of N-alkylated tetrahydroisoquinolines using as a solid support the compound 1a, a specific compound selected from the general formula (I). Scheme III demonstrates the diversity generation in the aromatic ring of tetrahydroisoquinoline while said compound is attached to the substrate (compound 1a).

In order to determine the amount of available double bonds and to optimise the reaction conditions, the secondary amine 5-ethoxy-1,2,3,4-tetrahydroisoquinoline (prepared in Example 9) was attached to compound 1a to give the corresponding compound 3, which then was quaternized with methyl iodide to give the corresponding quaternary ammonium ion 4. After cleavage with e.g. DIEA (diisopropylethyl amine), the tertiary amine 5-ethoxy-2-methyl-1,2,3,4-tetrahydroisoquinoline (5a) was released. This compound was analysed by HPLC using standard, which was made by a separate reaction in the solution phase. These analyses showed that i) the achieved loading was in the range of 200–270 μmol/g, ii) no UV absorbent side-products were observed, and iii) the highest yield was achieved when the quaternization step was made rapidly. The results are given in Table 1.

TABLE 1

Optimisation of reaction times for quaternising of a compound 3 of Scheme IIa and cleavage of 5a (5-ethoxy-2-methyl-1,2,3,4-tetrahydroisoquinoline) from compound 1a

| Entry | Quaternization time, h | Cleavage time h | Yield of 5a μmol/g |
|---|---|---|---|
| 1 | 18 | 18 | 212 |
| 2 | 18 | 4 | 223 |
| 3 | 18 | 1 | 240 |
| 4 | 6 | 18 | 230 |
| 5 | 1 | 18 | 270 |
| 6 | 0.5 | 0.5 | 252 |

To show the usability of compound (I) a small model library of substituted tetrahydroisoquinolines introducing diversity by three ways was made: i) by using different alkyl halides to quaternize the amine moiety of a compound 3, ii) by introducing an alkoxy substituent to the aromatic ring of tetrahydroisoquinoline, and iii) changing the position of the alkoxy group in the aromatic ring. Thus, tetrahydropyranyl protected 5- or 6-hydroxy-tetrahydroisoquinoline (2a and 2b, respectively; see Examples 5 and 6) was attached to compound 1a (see Example 13), the protection group was removed by acid methanolyze (see Example 14). The product obtained was subjected to Mitsunobu ether formation (ref. 5) (see Example 15) to introduce a desired alkoxy substituent. In this step, tributyl phosphine and 1,1'-(azodicarbonyl)dipiperidine (ref. 6) were used as reagents and gave a. 80–99% yield of 5a.

In the Examples presented below, Examples 1 to 9 relate to the synthesis of certain substituted tetrahydroisoquinoline derivatives and their starting materials, the nitrogen atom in the tetrahydroisoquinoline being unsubstituted. Example 10 concerns the synthesis of an N-substituted tetrahydroisoquinoline according to a previously known method. Examples 11 and 12 relate to the preparation of two alternative linkers bound to a solid support, Examples 13 to 17 relate to various steps in the synthesis of a tertiary amine based on the use of linkers bound to a solid support, and Examples 18 to 29 relate to certain alpha-2-receptor active N-substituted tetrahydroisoquinolines (tertiary amines) prepared according to the new method. Examples 30 to 94 describe further alpha-2-receptor active N-substituted tetrahydroisoquinolines.

EXAMPLE 1

5-Hydroxy-2-trifluoroacetyl-1,2,3,4-tetrahydroisoquinoline 2.35 g (15.9 mmol) 5-hydroxy-1,2,3,4-tetrahydroisoquinoline, 1.92 mL (19.0 mmol) methyltrifluoroacetate and 15 mL DMF were mixed and stirred for over night at room temperature. The reaction mixture was diluted with dichloromethane, washed with water containing one drop of dil. hydrochloric acid and with aqueous sodium chloride. After drying over $Na_2SO_4$ and evaporation to dryness, the product was purified by silicagel chromatography (system C). Yield quantitative. $^1$H NMR (CDCl$_3$, 400 MHz): 8.15 (1H, bd), 7.06 (1H, t, 8.1 Hz), 6.6–6.9 (2H, m), 4.75 (2H, ss), 3.86 (2H, m), 2.90 (2H, m).

EXAMPLE 2

6-Hydroxy-2-trifluoroacetyl-1,2,3,4-tetrahydroisoquinoline

The compound was prepared as described in Example 1, except that 6-hydroxy-1,2,3,4-tetrahydroisoquinoline was used. Yield 81%. $^1$H NMR (CDCl$_3$, 400 MHz): 6.97 (1H, t, 9.3 Hz), 6.77 (1H, dd, 8.3 Hz, 2.0 Hz), 6.69, (1H, dd, 8.8 Hz, 2.2 Hz), 4.70 (2H, d, 17.3 Hz), 3.82 (2H, m), 2.87 (2H, m).

EXAMPLE 3

5-(tetrahydropyran-2-yloxy)-2-trifluoroacetyl-1,2,3,4-tetrahydroisoquinoline 3.7 g (15.9 mmol) of 5-hydroxy-2-trifluoroacetyl-1,2,3,4-tetrahydroisoquinoline (Example 1) and 4.4 mL (47.7 mmol) 2,3-dihydropyrane were dissolved in dichloromethane and catalytic amount of p-toluenesulfonic acid monohydrate was added. After completion of the reaction (System A), the reaction mixture was diluted with dichloromethane, washed with water and aqueous sodium chloride. The solution was dried over $Na_2SO_4$, evaporated to dryness, and the product was purified by silicagel chromatography (System A). Yield 4.13 g, 79%. $^1$H NMR (CDCl$_3$, 400 MHz): 7.16 (1H, m), 7.00 (1H, m), 6.77 (1H, m), 5.45 (1H, m), 4.79 (2H, ss), 3.8 (3H, m), 3.6 (1H, m), 2.9 (4H, m).

EXAMPLE 4

6-(tetrahydropyran-2-yloxy)-2-trifluoroacetyl-1,2,3,4-tetrahydroisoquinoline

The compound was prepared as described in Example 3 except that the 6-hydroxysubstituted compound from Example 2 was used. Yield 38%. $^1$H NMR (CDCl$_3$, 400 MHz): 7.04 (1H, dd), 6.94 (1H, dd), 6.87 (1H, dd), 5.41 (1H, q), 4.70 (2H, ss), 3.87 (3H, m), 3.61 (1H, m), 2.91 (2H, m), 1.4–2.1 (6H, m).

EXAMPLE 5

5-(tetrahydropyran-2-yloxy)-1,2,3,4-tetrahydroisoquinoline (2a)

Excess of 2 mol L$^{-1}$ aqueous sodium hydroxide was added to a solution of 5-(tetrahydropyran-2-yloxy)-2-trifluoroacetyl-1,2,3,4-tetrahydroisoquinoline (Example 3) (4.1 g, 12.4 mmol) in dioxane. The mixture was stirred overnight, diluted with dichloromethane, washed with water and aqueous sodium chloride and evaporated. Yield 2.77 g, 96% $^1$H NMR (CDCl$_3$, 400 MHz): 7.07 (1H, t, 8.1 Hz), 6.92 (1H, d, 8.3 Hz), 6.66 (1H, d, 7.6 Hz), 5.43 (1H, t, 3.2 Hz), 3.99 (2H, s), 3.76 (1H, m), 3.61 (1H, m), 3.14 (2H, t, 6.1 Hz), 2,73 (2H, m), 1.5–2.1 (6H, m); $^{13}$C NMR (CDCl$_3$, 100 MHz): 154.6, 137.2, 126.0, 124.3, 119.1, 111.2, 95.8, 61.9, 48.3, 43.7, 30.5, 25.2, 23.5, 18.9; MS (EI, 70 eV): 233 (M$^+$, 8%), 148 (92%), 132 (23%), 120 (47%), 91 (16%), 85 (100%).

EXAMPLE 6

6-(tetrahydropyran-2-yloxy)-1,2,3,4-tetrahydroisoquinoline (2b)

The compound was prepared as described in Example 5 except that 6-(tetrahydropyran-2-yloxy)-2-trifluoroacetyl-1,2,3,4-tetrahydroisoquinoline from Example 4 was used. Yield quantitative. $^1$H NMR (CDCl$_3$, 400 MHz): 6.92 (1H, d, 8.5 Hz), 6.84 (1H, dd, 8.3 Hz, 2.4 Hz), 6.80 (1H, d, 2.4 Hz), 5.38 (1H, t, 3.2 Hz), 3.92 (2H, s), 3.85–4.00 (1H, m), 3.55–3.67 (1H, m), 3.11 (2H, t, 6.1 Hz), 2.76 (2H, t, 5.9 Hz), 1.5–2.1 (6H, m); $^{13}$C NMR (CDCl$_3$, 100 MHz): 155.2, 135.9, 129.2, 127.1, 116.8, 114.5, 96.4, 62.0, 47.8, 43.8, 30.4, 29.5, 25.3, 18.8.

EXAMPLE 7

2-t-butoxycarbonyl-5-hydroxy-1,2,3,4-tetrahydroisoquinoline 16.2 mL 2 L$^{-1}$ aqueous sodium hydroxyde and 3.6 g (16.4 mmol) di-tert-butyl dicarbonate were added to a solution of 5-hydroxy-1,2,3,4-tetrahydroisoquinoline hydrochloride (3 g, 16.2 mmol) in 50% (v/v) aqueous acetonitrile. The reaction mixture was left overnight and then diluted with ethyl acetate. The organic phase was separated, washed with aqueous sodium chloride, dried over $Na_2SO_4$, and evaporated to dryness. The product was purified by silicagel chromatography (System D). Yield 3.8 g, 95%. $^1$H NMR (CDCl$_3$, 500 MHz): 7.04 (1H, t, 7.8 Hz), 6.69 (1H, d, 7.6 Hz), 6.64 (1H, d, 7.9 Hz), 5.18 (1H, s), 4.55 (2H, s), 3.66 (2H, t, 5.6 Hz), 2.74 (2H, t, 6.0 Hz), 1.49 (9H, s).

EXAMPLE 8

2-t-butoxycarbonyl-5-ethoxy-1,2,3,4-tetrahydroisoquinoline 2.1 g (8.43 mmol) of 2-t-butoxycarbonyl-5-hydroxy-1,2,3,4-tetrahydroisoquinoline (Example 7), 2.77 g (10.5 mmol) triphenylphosphine and 0.75 mL (12.6 mmol) ethanol were dissolved in dry tetrahydrofuran and 1.63 mL (10.5 mmol) diethylazodicarboxylate was added dropwise. After completion of the reaction (tlc, 1% MeOH), the mixture was diluted with dichloromethane, washed with aqueous sodium bicarbonate and with aqueous sodium chloride, evaporated to dryness and purified by silicagel chromathography (System B). Yield 1.55 g, 66%. $^1$H NMR (CDCl$_3$): 7.12 (1H, t, 8.1 Hz), 6.69 (2H, t, 8.1 Hz), 4.55 (2H, s), 4.02 (2H, q, 6.8 Hz), 3.63 (2H, t, 5.6 Hz), 2.76 (2H, t, 5.9 Hz), 1.48 (9H, s), 1.41 (3H, t, 7.1 Hz).

EXAMPLE 9

5-ethoxy-1,2,3,4-tetrahydroisoquinoline

Excess of 3 mol L$^{-1}$ hydrochloric acid in ethanol was added to a solution of 2-t-butoxycarbonyl-5-ethoxy-1,2,3,4- tetrahydroisoquinoline (Example 8) (1.55 g, 5.6 mmol) in ethanol. After 3 hours, the solution was evaporated to dryness, and the hydrochloride salt of 5-ethoxy-1,2,3,4-tetrahydroisoquinoline was dissolved in water. The solution was made strongly alkaline with sodium hydroxide, and the product was extracted in dichloromethane, dried over $Na_2SO_4$, and evaporated. The product was purified by recrystallization from absolute ethanol. Yield 0.69 g, 71%. $^1$H NMR (DMSO-$d_6$, 500 MHz): 7.02 (1H, t, 7.8 Hz). 6.70 (1H, d, 8.0 Hz), 6.57 (1H, d, 7.2 Hz), 3.98 (2H, q, 6.9 Hz), 3.77 (2H, s), 3.24 (2H, s), 2.91 (2H, s), 1.31 (3H, t, 6.9 Hz); $^{13}$C NMR (DMSO-$d_6$, 120 MHz): 156.1, 137.5, 125.7, 123.5, 118.1, 108.2, 62.9, 47.7, 43.0, 23.1, 14.7; MS(EI$^+$): 177 (95%, M+), 148 (100%), 132 (25%), 120 (43%), 104 (56%), 91 (33%).

EXAMPLE 10

5-ethoxy-2-methyl-1,2,3,4-tetrahydroisoquinoline (5a)

To the solution of 5-hydroxy-2-methyl-1,2,3,4-tetrahydroisoquinoline (0.5 g, 3.07 mmol), triphenylphosphine (1.0 g, 3.83 mmol) and ethanol (0.27 mL, 4.61 mmol) in dry tetrahydrofurane 0.597 mL (3.83 mmol) diethyldiazodicarboxylate was added dropwise. After the reaction mixture was stirred at r.t. overnight, it was diluted with dichloromethane, washed with water, and the product was extracted into dilute aqueous hydrochloric acid solution, which was washed with dichloromethane. The aqueous phase was made alkaline with aqueous sodium hydroxide, and extracted with dichloromethane. The dichloromethane solution was dried over $Na_2SO_4$ and evaporated. The product was purified by silicagel chromathography (System E) and recrystallised from absolute ethanol. Yield 0.586 g, 48%. $^1$H NMR (CDCl$_3$): 7.07 (1H, t, 8.1 Hz), 6.64 (2H, m), 4.01 (2H, q, 7.1 Hz), 3.55 (2H, s), 2.81 (2H, t, 6.1 Hz), 2.67 (2H, t, 6.1 Hz), 2.44 (3H, s), 1.40 (3H, t, 6.8 Hz). $^{13}$C NMR (CDCl$_3$): 156.5, 135.9, 126.1, 123.0, 118.4, 108.3, 63.3, 57.9, 52.7, 46.0, 23.8, 14.9; MS (EI$^+$): 191 (83%), 190 (100%), 162 (15%), 160 (16%), 148 (61%), 120 (28%), 104 (48%); R$_t$ (HPLC)=8.1 min.

EXAMPLE 11

Synthesis of Solid Support 1a (Scheme IIa)

Hydroxymethylated polystyrene beads (0.2 g) were suspended in dry dichloromethane (2 mL). DBU (0.1 mL) and divinyl sulfone (0.2 mL, predissolved in 1 mL of dichloromethane) were added. The mixture was shaken overnight at room temperature, filtered, washed with dichloromethane (3×3 mL) and with methanol (3×3 mL), and dried in a reduced pressure.

EXAMPLE 12

Synthesis of Solid Support 1b (Scheme IIb)

Aminomethylated polystyrene beads or Tentagel™ NH (0.2 g) were suspended in dry dichloromethane (2 mL) containing one drop of bromothymol blue indicator in DMF. 200 μL vinylsulfonyl chloride was added, and then diluted DBU was introduced in small portions until blue color of indicator was achieved. The solid support beads were filtered, washed with dichloromethane (3×3 mL) and with methanol (3×3 mL), and dried in a reduced pressure.

EXAMPLE 13

Synthesis of Compound 3a (Scheme IIa, III)

The solid support 1a of Example 11 (50 mg) was suspended in DMF and compound 2a of Example 5 (0.25 mmol) was added. The mixture was shaken at room temperature for 4 days, filtered, washed with DMF (3×3 mL), with dichloromethane (3×3 mL) and with methanol (3×3 mL), and dried in a reduced pressure.

EXAMPLE 14

Synthesis of 3b, Scheme III

The compound 3a (Example 13) (50 mg) was suspended in the solution containing 1 mL dichloromethane, 1 mL methanol and 0.2 mL trifluoroacetic acid. The mixture was shaken overnight at room temperature, filtered, washed with dichloromethane (3×3 mL) and with methanol (3×3 mL), and dried in a reduced pressure.

EXAMPLE 15

Synthesis of 3c of Scheme III (Mitsunobu Reaction on Solid Support)

The compound 3b from Example 14 (15 mg) was placed in small polypropylene column, which was attached two 2 mL syringes, one of those loaded with 1 mL solution of 0.1 mol L$^{-1}$ tributylphosphine and 1 mmol of ethanol in dry tetrahydrofurane. The solution was flushed through the column for several times, the solution was withdrawn into one of the syringes, and the other syringe was used to add 0.1 μmol 1,1'-(azodicarbonyl)-dipiperidine in 0.6 mL dry tetrahydrofurane. The reaction mixture was left for 4 h at room temperature with occasional flushing. The solution was withdrawn from the column and it was washed with dichloromethane (3×3 mL) and with methanol (3×3 mL), and dried in a reduced pressure.

EXAMPLE 16

Synthesis of Compound 4a of Scheme IIa (Quaternization of Solid Support Bound Secondary Amine)

The reaction column containing the compound 3c of Example 15 (15 mg) was attached two syringes, one of those containing 100 μL iodomethane (1.6 mmol) in DMF (1 mL). The solution was flushed through the column several times, and the reaction mixture was left for 0.5 h at room temperature. The solution was withdrawn from the column, and it was washed with DMF (3×3 mL), with dichloromethane (3×3 mL) and with methanol ( 3×3 mL), and dried in a reduced pressure.

EXAMPLE 17

Synthesis of 5-ethoxy-2-methyl-1,2,3,4-tetrahydroisoquinoline (Compound 5a of Scheme IIa)

The compound 4a of Example 16 was suspended in dichloromethane containing diisopropylethyl amine (0.05 mL of DIEA in 1.0 mL dichloromethane), and the mixture was shaken for 1 h at room temperature. The dichloromethane solution was separated, the support was washed with dichloromethane (3×3 mL) and with methanol (3×3 mL). All solutions were combined and evaporated. R$_t$=8.1 min. MS (EI$^+$): 191 (83%), 190 (100%),162 (15%), 160 (16%), 148 (61%), 120 (28%).

In the Examples listed below the alpha-2-receptor active compounds 5b to 5m in Table 2 were prepared according to the procedure described in Example 17 and the foregoing Examples using as compound 2a 1,2,3,4- tetrahydroisoquinoline substituted with a tetrahydropyran-2-yloxy group in the appropriate position, substituting the tetrahydropyran-2-yloxy group with hydroxy and subjecting said hydroxysubstituted compound to a Mitsunobu reaction using an appropriate alcohol to give the desired ether group in the compound 3, which then was quaternized and cleavaged to yield the tertiary amine.

EXAMPLE 18

5-(5-cyano-1-pentyloxy)-2-methyl-1,2,3,4-tetrahydroisoquinoline (5b)

MS: 257 (100, $M^+$–1), 215 (30), 162 (31), 146 (12), 120 (51); $^1$H NMR (400 MHz, CDCl$_3$): 7.07 (1H, t, J=8.0), 6.64 (2H, d, J=8.1), 3.97 (2H, t, J=6.1), 3.55 (2H, s), 2.79 (2H, t, J=6.1), 2.68 (2H, t, J=6.3), 2.45 (3H, s), 2.38 (2H, t, J=7.1), 1.79–1.96 (2H, m), 1.71–1.79 (2H, m), 1.60–1.70 (2H, m); $R_f$: 0.42 (8% MeOH/CH$_2$Cl$_2$).

EXAMPLE 19

6-(5-cyano-1-pentyloxy)-2-methyl-1,2,3,4-tetrahydroisoquinoline (5c)

MS: 257 (100, $M^+$–1), 215 (27), 162 (24), 146 (6), 120 (40); $R_f$: 0.40 (8% MeOH/CH$_2$Cl$_2$).

EXAMPLE 20

5-(3,4-difluorophenylmethoxy)-2-methyl-1,2,3,4-tetrahydroisoquinoline (5d)

MS: 289 (50, $M^+$), 162 (33), 146 (6), 127 (100); $^1$H NMR (400 MHz, CDCl$_3$): 7.06–7.28 (4H, m), 6,66–6.69 (2H, m), 5.01 (2H, s), 3.57 (2H, s), 2.87 (2H, t, J=6.1), 2.70 (2H, t, J=6.1), 2.46 (3H, s); $R_f$: 0.48 (8% MeOH/CH$_2$Cl$_2$).

EXAMPLE 21

6-(3,4-difluorophenylmethoxy)-2-methyl-1,2,3,4-tetrahydroisoquinoline (5e)

MS: 288 (69, $M^+$–1), 161 (27), 127 (100); $R_f$: 0.47 (8% MeOH/CH$_2$Cl$_2$).

EXAMPLE 22

8-(3,4-difluorophenylmethoxy)-2-methyl-1,2,3,4-tetrahydroisoquinoline (5f)

MS 288 (30, $M^+$–1), 161 (100), 127 (72); $R_f$: 0.56 (8% MeOH/CH$_2$Cl$_2$).

EXAMPLE 23

5-butoxy-2-propyl-1,2,3,4-tetrahydroisoquinoline (5g)

$^1$H NMR (400 MHz, CDCl$_3$): 7.07 (1H, t, J=8.1), 6.62–6.67 (2H, m), 3.95 (2H, t, J=6.3), 3.61 (2H, s), 2.74–2.80 (4H, m), 2.45–2.49 (2H, m), 1.73–1.81 (2H, m), 1.58–1.68 (2H, m), 1.38–1.55 (2H, m), 0.93–1.05 (6H, m); $^{13}$C NMR: 12.0, 13.9, 19.4, 20.0, 23.2, 31.5, 50.8, 55.9, 60.3, 67.5, 108.4, 118.4, 123.2, 126.4, 135.5, 156.7.

EXAMPLE 24

5-cyclohexylmethoxy-2-methyl-1,2,3,4-tetrahydroisoquinoline (5h)

MS: 258 (92, $M^+$–1), 216 (21), 162 (34), 146 (18), 120 (100); $R_f$: 0.43 (8% MeOH/CH$_2$Cl$_2$).

EXAMPLE 25

6-cyclohexylmethoxy-2-methyl-1,2,3,4-tetrahydroisoquinoline (5i)

MS: 258 (100, $M^+$–1), 216 (13), 162 (49), 146 (5), 120 (57); $R_f$: 0.39 (8% MeOH/CH$_2$Cl$_2$).

EXAMPLE 26

8-cyclohexylmethoxy-2-methyl-1,2,3,4-tetrahydroisoquinoline (5j)

MS: 258 (100, $M^+$–1), 216 (13), 162 (90), 146 (8), 120 (65); $R_f$: 0.57 (8% MeOH/CH$_2$Cl$_2$).

EXAMPLE 27

5-tetradecanyloxy-2-methyl-1,2,3,4-tetrahydroisoquinoline (5k)

MS:358 (100, $M^+$–1), 316 (10), 162 (23), 146 (18), 120 (36); $^1$H NMR (400 MHz, CDCl$_3$): 7.07 (1H, t, J=7.8), 6.63 (2H, t, J=8.3), 3.94 (2H, t, J=6.3), 3.55 (2H, s), 2.80 (2H, t, J=6.1), 2.67 (2H, t, J=6.1), 2.44 (3H, s), 1.74–1.81 (2H, m), 1.45 (2H, m), 1.26 (10OH, m), 0.88 (3H, t, J=7.1); $R_f$: 0.50 (8% MeOH/CH$_2$Cl$_2$).

EXAMPLE 28

6-tetradecanyloxy-2-methyl-1,2,3,4-tetrahydroisoquinoline (5l)

MS:359 (100, $M^+$), 316 (8), 162 (19), 120 (15); $R_f$: 0.51 (8% MeOH/CH$_2$Cl$_2$).

EXAMPLE 29

8-tetradecanyloxy-2-methyl-1,2,3,4-tetrahydroisoquinoline (5m)

MS: 358 (100, $M^+$–1), 316 (6), 162 (37), 146 (6), 120 (23); $R_f$: 0.49 (8% MeOH/CH$_2$Cl$_2$).

EXAMPLE 30

5-(4-tert-butylphenoxy)-2-methyl-1,2,3,4-tetrahydroisoquinoline

MS: 309 ($M^+$, 22), 162 (10), 147 (100), 132 (18); $R_f$: 0.48 (8% MeOH/CH$_2$Cl$_2$).

EXAMPLE 31

2-methyl-5-(4-phenoxybutoxy)-1,2,3,4-tetrahydroisoquinoline

MS: 311 ($M^+$, 100), 162 (26), 149 (56), 120 (12); $R_f$: 0.47 (8% MeOH/CH$_2$Cl$_2$).

EXAMPLE 32

5-(2-cyanophenylmethoxy)-2-methyl-1,2,3,4-tetrahydroisoquinoline

MS: 277 ($M^+$–1, 87), 235 (26), 162 (100), 146 (11); $R_f$: 0.47 (8% MeOH/CH$_2$Cl$_2$).

EXAMPLE 33

2-methyl-5-(3-phthaloylpropoxy)-1,2,3,4-tetrahydroisoquinoline

MS: 350 ($M^+$, 69), 188 (100), 162 (25), 160 (60), 146 (12), 130 (15); $R_f$: 0.34 (8% MeOH/CH$_2$Cl$_2$).

EXAMPLE 34

2-methyl-5-(4-phthaloylbutoxy)-1,2,3,4-tetrahydroisoquinoline

MS: 364 (M$^+$, 85), 202 (44), 162 (41), 160 (100), 146 (13), 130 (13), 120 (15); R$_f$: 0.48 (8% MeOH/CH$_2$Cl$_2$).

EXAMPLE 35

5-(2-(2,5,5-trimethyl-1,3-dioxan-2-yl)-ethoxy)-2-methyl-1,2,3,4-tetrahydroisoquinoline MS: 318 (M$^+$–1, 20), 162 (100), 146 (13), 120 (62); R$_f$: 0.22 (8% MeOH/CH$_2$Cl$_2$).

EXAMPLE 36

5-((R)-3-hydroxy-2-methylpropoxy)-2-methyl-1,2,3,4-tetrahydroisoquinoline

MS: 234 (M$^+$–1, 85), 192 (21), 162 (58), 146 (18), 120 (100); R$_f$: 0.30 (8% MeOH/CH$_2$Cl$_2$).

EXAMPLE 37

5-(2-(1,3-dioxan-2-yl)-ethoxy-2-methyl-1,2,3,4-tetrahydroisoquinoline

MS: 276 (M$^+$–1, 100), 234 (10), 218 (16), 162 (21), 146 (19); R$_f$: 0.50 (8% MeOH/CH$_2$Cl$_2$).

EXAMPLE 38

5-(2-indol-3-ylethoxy)-2-methyl-1,2,3,4-tetrahydroisoquinoline

MS: 306 (M$^+$, 63), 162 (35), 144 (100), 130 (15).

EXAMPLE 39

2-methyl-5-(4-nitrophenylmethoxy)-1,2,3,4-tetrahydroisoquinoline

MS: 297 (M$^+$–1, 100), 255 (23), 162 (79), 146 (16), 136 (20).

EXAMPLE 40

5-benzyloxy-2-methyl-1,2,3,4-tetrahydroisoquinoline

MS: 253 (M$^+$, 43), 162 (23), 91 (100); R$_f$: 0.41 (8% MeOH/CH$_2$Cl$_2$).

EXAMPLE 41

5-(4-chlorophenylmethoxy)-2-methyl-1,2,3,4-tetrahydroisoquinoline

MS: 287 (M$^+$, 48), 162 (38), 125 (100); R$_f$: 0.48 (8% MeOH/CH$_2$Cl$_2$).

EXAMPLE 42

6-(4-tert-butylphenoxy)-2-methyl-1,2,3,4-tetrahydroisoquinoline

MS: 308 (M$^+$–1, 15), 147 (100), 132 (14); R$_f$: 0.40 (8% MeOH/CH$_2$Cl$_2$).

EXAMPLE 43

6-(3-methoxyacetophenoxy)-2-methyl-1,2,3,4-tetrahydroisoquinoline

MS: 310 (M$^+$–1, 100), 268 (21), 162 (34), 149 (17), 135 (52), 120 (10); R$_f$: 0.39 (8% MeOH/CH$_2$Cl$_2$).

EXAMPLE 44

2-methyl-6-(4-phenoxybutoxy)-1,2,3,4-tetrahydroisoquinoline

MS: 310 (M$^+$–1, 100), 162 (21), 149 (34); R$_f$: 0.46 (8% MeOH/CH$_2$Cl$_2$).

EXAMPLE 45

6-(2-cyanophenylmethoxy)-2-methyl-1,2,3,4-tetrahydroisoquinoline

MS: 277 (M$^+$–1, 100), 235 (26), 162 (43), 132 (11), 116 (48); R$_f$: 0.46 (8% MeOH/CH$_2$Cl$_2$).

EXAMPLE 46

2-methyl-6-(4-nitrophenylmethoxy)-1,2,3,4-tetrahydroisoquinoline

MS: 297 (M$^+$–1, 100), 255 (20), 162 (32), 136 (20); R$_f$: 0.39 (8% MeOH/CH$_2$Cl$_2$).

EXAMPLE 47

2-methyl-6-(3-phthaloylpropoxy)-1,2,3,4-tetrahydroisoquinoline

MS: 349 (M$^+$–1, 55), 188 (100), 162 (24), 160 (52), 146 (11), 130 (13); R$_f$: 0.26 (8% MeOH/CH$_2$Cl$_2$).

EXAMPLE 48

2-methyl-6-(4-phthaloylbutoxy)-1,2,3,4-tetrahydroisoquinoline

MS: 363 (M$^+$–1, 98), 202 (53), 162 (71), 160 (100), 146 (19), 130 (14), 120 (23); R$_f$: 0.39 (8% MeOH/CH$_2$Cl$_2$).

EXAMPLE 49

6-(2-(2,5,5-trimethyl-1,3-dioxan-2-yl)-ethoxy)-2-methyl-1,2,3,4-tetrahydroisoquinoline MS: 318 (M$^+$–1, 100), 304 (14), 232 (53), 162 (30), 129 (27), 120 (11); R$_f$: 0.29 (8% MeOH/CH$_2$Cl$_2$).

EXAMPLE 50

6-benzyloxy-2-methyl-1,2,3,4-tetrahydroisoquinoline

MS: 252 (M$^+$–1, 27), 91 (100); R$_f$: 0.50 (8% MeOH/CH$_2$Cl$_2$).

EXAMPLE 51

6-(4-chlorophenylmethoxy)-2-methyl-1,2,3,4-tetrahydroisoquinoline

MS: 286 (M$^+$–1, 67), 162 (22), 125 (100); R$_f$: 0.44 (8% MeOH/CH$_2$Cl$_2$).

EXAMPLE 52

6-(2-(1,3-dioxan-2-yl)-ethoxy-2-methyl-1,2,3,4-tetrahydroisoquinoline

MS: 276 (M$^+$–1, 100), 234 (11), 218 (26), 162 (30), 120 (16); R$_f$: 0.24 (8% MeOH/CH$_2$Cl$_2$).

EXAMPLE 53

6-(2-indol-3-ylethoxy)-2-methyl-1,2,3,4-tetrahydroisoquinoline

MS: 306 (M$^+$, 58), 162 (79), 144 (100), 130 (15); R$_f$: 0.27 (8% MeOH/CH$_2$Cl$_2$).

EXAMPLE 54

6-butoxy-2-methyl-1,2,3,4-tetrahydroisoquinoline

MS: 218 ($M^+$–1, 100), 176 (31), 162 (33), 120 (50); $R_f$: 0.41 (8% MeOH/$CH_2Cl_2$).

EXAMPLE 55

2-methyl-6-propoxy-1,2,3,4-tetrahydroisoquinoline

MS: 204 ($M^+$–1, 100), 162 (64), 120 (40); $R_f$: 0.50 (8% MeOH/$CH_2Cl_2$).

EXAMPLE 56

8-(4-tert-butylphenoxy)-2-methyl-1,2,3,4-tetrahydroisoquinoline

MS: 308 ($M^+$–1, 11), 176 (13), 162 (67), 147 (100), 132 (30); $R_f$: 0.45 (8% MeOH/$CH_2Cl_2$).

EXAMPLE 57

2-methyl-8-(4-phenoxybutoxy)-1,2,3,4-tetrahydroisoquinoline

MS: 310 ($M^+$–1, 100), 162 (61), 149 (30), 146 (15); $R_f$: 0.52 (8% MeOH/$CH_2Cl_2$).

EXAMPLE 58

8-(2-cyanophenylmethoxy)-2-methyl-1,2,3,4-tetrahydroisoquinoline

MS: 277 ($M^+$–1, 45), 162 (100); $R_f$: 0.45 (8% MeOH/$CH_2Cl_2$).

EXAMPLE 59

2-methyl-8-(4-nitrophenylmethoxy)-1,2,3,4-tetrahydroisoquinoline

MS: 297 ($M^+$–1, 58), 162 (42); $R_f$: 0.40 (8% MeOH/$CH_2Cl_2$).

EXAMPLE 60

2-methyl-8-(3-phthaloylpropoxy)-1,2,3,4-tetrahydroisoquinoline

MS: 350 ($M^+$, 22), 188 (58), 162 (100), 160 (75), 146 (20), 130 (17), 120 (35); $R_f$: 0.55 (8% MeOH/$CH_2Cl_2$).

EXAMPLE 61

2-methyl-8-(4-phthaloylbutoxy)-1,2,3,4-tetrahydroisoquinoline

MS: 364 ($M^+$, 82), 349 (48), 202 (34), 162 (100), 160 (98), 146 (34), 130 (16), 120 (16); $R_f$: 0.53 (8% MeOH/$CH_2Cl_2$).

EXAMPLE 62

8-benzyloxy-2-methyl-1,2,3,4-tetrahydroisoquinoline

MS: 252 ($M^+$–1, 29), 162 (72), 120 (15), 91 (93); $R_f$: 0.53 (8% MeOH/$CH_2Cl_2$).

EXAMPLE 63

8-(4-chlorophenylmethoxy)-2-methyl-1,2,3,4-tetrahydroisoquinoline

MS: 286 ($M^+$–1, 27), 162 (51), 125 (65); $R_f$: 0.43 (8% MeOH/$CH_2Cl_2$).

EXAMPLE 64

8-((R)-3-hydroxy-2-methylpropoxy)-2-methyl-1,2,3,4-tetrahydroisoquinoline

MS: 234 ($M^+$–1, 42), 162 (100), 146 (11), 120 (63); $R_f$: 0.39 (8% MeOH/$CH_2Cl_2$).

EXAMPLE 65

8-(2-(1,3-dioxan-2-yl)-ethoxy-2-methyl-1,2,3,4-tetrahydroisoquinoline

MS: 276 ($M^+$–1, 25), 218 (100), 162 (27), 146 (12); $R_f$: 0.47 (8% MeOH/$CH_2Cl_2$).

EXAMPLE 66

8-(2-indol-3-ylethoxy)-2-methyl-1,2,3,4-tetrahydroisoquinoline

MS: 306 ($M^+$), 162 (100), 144 (51), 130 (21); $R_f$: 0.28 (8% MeOH/$CH_2Cl_2$).

EXAMPLE 67

5-butoxy-2-methyl-1,2,3,4-tetrahydroisoquinoline

MS: 218 ($M^+$–1, 100), 176 (48), 162 (25), 146 (15), 120 (89); $R_f$: 0.46 (8% MeOH/$CH_2Cl_2$).

EXAMPLE 68

2-methyl-5-propoxy-1,2,3,4-tetrahydroisoquinoline

MS: 204 ($M^+$–1, 82), 162 (72), 146 (23), 120 (100); $R_f$: 0.42 (8% MeOH/$CH_2Cl_2$).

EXAMPLE 69

2-methyl-5-(2-phenoxyethoxy)-1,2,3,4-tetrahydroisoquinoline

MS: 282 ($M^+$–1, 100), 162 (21), 146 (36), 120 (18); $R_f$: 0.46 (8% MeOH/$CH_2Cl_2$).

EXAMPLE 70

2-methyl-5-phenylsulfinylmethoxy-1,2,3,4-tetrahydroisoquinoline

MS: 301 ($M^+$, 10), 176 (100), 162 (8), 146 (13); $R_f$: 0.41 (8% MeOH/$CH_2Cl_2$).

EXAMPLE 71

2-methyl-5-(3-phenoxyproxy)-1,2,3,4-tetrahydroisoquinoline

MS: 296 ($M^+$–1, 100), 162 (24), 146 (14), 135 (18), 120 (20); $R_f$: 0.47 (8% MeOH/$CH_2Cl_2$).

EXAMPLE 72

2-methyl-5-(2-tetrahydropyran-2-yloxyethoxy)-1,2,3,4-tetrahydroisoquinoline

MS: 290 ($M^+$–1, 59), 206 (20), 162 (22), 146 (14); $R_f$: 0.36 (8% MeOH/$CH_2Cl_2$).

EXAMPLE 73

2-methyl-6-(2-phenoxyethoxy)-1,2,3,4-tetrahydroisoquinoline

MS: 282 ($M^+$–1, 100), 240 (23), 162 (26), 120 (29); $R_f$: 0.48 (8% MeOH/$CH_2Cl_2$).

EXAMPLE 74

2-methyl-6-phenylsulfinylmethoxy-1,2,3,4-tetrahydroisoquinoline

MS: 301 (M$^+$, 8), 176 (100), 162 (8), 146 (29); R$_f$: 0.58 (8% MeOH/CH$_2$Cl$_2$).

EXAMPLE 75

2-methyl-6-(3-phenoxyproxy)-1,2,3,4-tetrahydroisoquinoline

MS: 296 (M$^+$−1, 100), 254 (12), 162 (28), 135 (15), 120 (28); R$_f$: 0.49 (8% MeOH/CH$_2$Cl$_2$).

EXAMPLE 76

2-methyl-6-(2-tetrahydropyran-2-yloxyethoxy)-1,2,3,4-tetrahydroisoquinoline

MS: 290 (M$^+$−1, 100), 206 (29), 162 (62), 146 (10), 129 (31), 120 (28); R$_f$: 0.30 (8% MeOH/CH$_2$Cl$_2$).

EXAMPLE 77

8-butoxy-2-methyl-1,2,3,4-tetrahydroisoquinoline

MS: 218 (M$^+$−1, 100), 176 (29), 162 (41), 120 (58); R$_f$: 0.54 (8% MeOH/CH$_2$Cl$_2$).

EXAMPLE 78

2-methyl-8-propoxy-1,2,3,4-tetrahydroisoquinoline

MS: 204 (M$^+$−1, 100), 162 (78), 146 (11), 120 (60); R$_f$: 0.43 (8% MeOH/CH$_2$Cl$_2$).

EXAMPLE 79

2-methyl-8-(2-phenoxyethoxy)-1,2,3,4-tetrahydroisoquinoline

MS: 282 (M$^+$−1, 100), 162 (37), 146 (29), 120 (12); R$_f$: 0.44 (8% MeOH/CH$_2$Cl$_2$).

EXAMPLE 80

2-methyl-8-(3-phenoxyproxy)-1,2,3,4-tetrahydroisoquinoline

MS: 296 (M$^+$−1, 100), 162 (57), 146 (23), 135 (11), 120 (14); R$_f$: 0.57 (8% MeOH/CH$_2$Cl$_2$).

EXAMPLE 81

2-methyl-8-(2-tetrahydropyran-2-yloxyethoxy)-1,2,3,4-tetrahydroisoquinoline

MS: 291 (M$^+$, 10), 206 (100), 162 (33); R$_f$: 0.35 (8% MeOH/CH$_2$Cl$_2$).

EXAMPLE 82

2-methyl-6-(4-phenylbutoxy)-1,2,3,4-tetrahydroisoquinoline $^1$H NMR (CDCl$_3$, 400 MHz): 7.31–7.15 (5H, m), 6.91 (1H, d, J=8,4 Hz), 6.66 (1H, dd, J=2.6 Hz, J=8.4 Hz), 6.62 (1H, d, J=2.6 Hz), 3.93 (2H, m), 3.51 (2H, s), 2.88 (2H, t, J=6.0 Hz), 2.71–2.60 (4H, m), 2.44 (3H, s), 1.85–1.75 (4H, m); $^{13}$C NMR (CDCl$_3$, 100 MHz): 157.4, 142.3, 134.9, 128.4, 128.3, 127.3, 126.8, 125.8, 113.9, 112.6, 67.7, 57.5, 52.8, 46.1, 35.6, 29.5, 28.9, 27.9.

EXAMPLE 83

2-methyl-5-(4-phenylbutoxy)-1,2,3,4-tetrahydroisoquinoline $^1$H NMR (CDCl$_3$, 400 MHz): 7.32–7.15 (5H, m), 7.06 (1H, t, J=7.8 Hz), 6.66–6.60 (2H, m), 3.97 (2H, m), 3.55 (2H, s), 2.80 (2H, t, J=6.0 Hz), 2.72–2.60 (4H, m), 2.44 (3H, s), 1.87–1.76 (4H, m), $^{13}$C NMR (CDCl$_3$, 100 MHz): 156.6, 142.3, 136.0, 128.4, 128.3, 126.1, 125.8, 123.0, 118.4, 108.2, 67.5, 57.9, 52.7, 46.0, 35.6, 28.9, 27.9, 23.8.

EXAMPLE 84

2-methyl-6-(3-methylpropoxy)-1,2,3,4-tetrahydroisoquinoline $^1$H NMR (CDCl$_3$, 400 MHz): 6.91 (1H, d, J=8,4 Hz), 6.68 (1H, dd, J=2.6 Hz, J=8.4 Hz), 6.62 (1H, d, J=2.6 Hz), 3.68 (2H, d, J=6.6 Hz), 3.51 (2H, s), 2.89 (2H, t, J=5.9 Hz), 2.66 (2H, t, J=6.0 Hz), 2.44 (3H, s), 2.05 (1H, m), 1.00 (6H, d, J=6.7 Hz); $^{13}$C NMR (CDCl$_3$, 100 MHz): 157.6, 134.9, 127.2, 126.7, 113.9, 112.6, 74.5, 57.5, 52.9, 46.1, 29.5, 28.3, 19.3.

EXAMPLE 85

2-methyl-5-(3-methylpropoxy)-1,2,3,4-tetrahydroisoquinoline $^1$H NMR (CDCl$_3$, 400 MHz): 7.03 (1H, t, J=8,1 Hz), 6.55–6.65 (2H, m), 3.71 (2H, d, J=6.3 Hz), 3.55 (2H, s), 2.83 (2H, t, J=6.1 Hz), 2.68 (2H, t, J=6.3 Hz), 2.45 (3H, s), 2.09 (1H, m), 1.02 (6H, d, J=6.6 Hz); $^{13}$C NMR (CDCl$_3$, 100 MHz): 156.7, 136.0, 126.1, 123.0, 118.3, 108.2, 74.1, 57.9, 52.7, 46.1, 28.4, 23.8, 19.3.

EXAMPLE 86

2-methyl-5-((E)-3-methylprop-2-en-1-yloxy)-1,2,3,4-tetrahydroisoquinoline $^1$H NMR (CDCl$_3$, 400 MHz): 7.06 (1H, t, J=7.8 Hz), 6.60–6.70 (2H, m), 5.90–5.60 (2H, m), 4.43–4.47 (2H, m), 3.55 (2H, s), 2.82 (2H, t, J=6.0 Hz), 2.68 (2H, t, J=6.2 Hz), 2.44 (3H, s), 1.73–1.77 (3H, m); $^{13}$C NMR (CDCl$_3$, 100 MHz): 156.3, 135.9, 129.4, 126.4, 126.0, 123.1, 118.6, 108.

EXAMPLE 87

6-(6-hydroxyhexyloxy)-2-methyl-1,2,3,4-tetrahydroisoquinoline

MS: 262 (100, M$^+$−1), 220 (12), 162 (36), 120 (45); $^1$H NMR (400 MHz, CDCl$_3$): 6.92 (d, 1H, J=8.5 Hz), 6.68 (d+d, 1H, J=2.4 Hz, J=8.5 Hz), 6.63 (d, 1H, J=2.2 Hz), 3.92 (t, 2H, J=6.6 Hz), 3.65 (t, 2H, J=6.6 Hz), 3.51 (s, 2H), 2.89 (t, 2H, J=5.8 Hz), 2.65 (t, 2H, J=5.8 Hz), 2.44 (s, 3H), 1.74–1.81 (m, 2H), 1.56–1.63 (m, 2H), 1.38–1.52 (m, 4H); $^{13}$C NMR (100 MHz, CDCl$_3$): 25.6, 25.9, 29.3, 29.5, 32.7, 46.1, 52.9, 57.5, 62.8, 67.8, 112.5, 113.9, 126.8, 127.3, 134.9, 157.5.

EXAMPLE 88

6-(5-hydroxypentyloxy)-2-methyl-1,2,3,4-tetrahydroisoquinoline

MS: 248 (100, M$^+$−1), 206 (11), 162 (49), 120 (57); $^1$H NMR (400 MHz, CDCl$_3$): 6.92 (d, 1H, J=8.3 Hz), 6.68 (d+d, 1H, J=2.4 Hz, J=8.6 Hz), 6.63 (d, 1H, J=2.2 Hz), 3.92 (t, 2H, J=6.4 Hz), 3.65 (t, 2H, J=6.4 Hz), 3.51 (s, 2H), 2.89 (t, 2H,

J=5.9 Hz), 2.66 (t, 2H, J=5.9 Hz), 2.44 (s, 3H), 1.75–1.82 (m, 2H), 1.59–1.66 (m, 2H), 1.45–1.55 (m, 2H); $^{13}$C NMR (100 MHz, CDCl$_3$): 22.4, 29.1, 29.5, 32.5, 46.1, 52.8, 57.5, 62.7, 67.8, 112.5, 113.9, 126.8, 127.3, 134.9, 157.4.

EXAMPLE 89

6-(4-hydroxybutoxy)-2-methyl-1,2,3,4-tetrahydroisoquinoline

MS: 234 (93, M$^+$–1), 192 (7), 162 (63), 120 (100); $^1$H NMR (500 MHz, CDCl$_3$): 6.92 (d, 1H, J=8.4 Hz), 6.69 (d+d, 1H, J=2.6 Hz, J=8.4 Hz), 6.64 (d, 1H, J=2.5 Hz), 3.97 (t, 2H, J=6.3 Hz), 3.71 (t, 2H, J=6.3 Hz), 3.52 (s, 2H), 2.89 (t, 2H, J=6.0 Hz), 2.67 (t, 2H, J=6.0 Hz), 2.44 (s, 3H), 1.84–1.89 (m, 2H), 1.72–1.77 (m, 2H); $^{13}$C NMR (100 MHz, CDCl$_3$): 25.9, 29.4, 29.6, 46.0, 52.7, 57.4, 62.6, 67.9, 112.5, 114.0, 126.8, 127.3, 134.9, 157.4.

EXAMPLE 90

6-(3-hydroxypropoxy)-2-methyl-1,2,3,4-tetrahydroisoquinoline

MS: 220 (100, M$^+$–1), 178 (29), 162 (46), 120 (50); $^1$H NMR (400 MHz, DMSO-d$_6$): 6.87 (d, 1H, J=8.3 Hz), 6.6 (m, 2H), 3.92 (t, 2H, J=6.3 Hz), 3.49 (t, 2H, J=6.1 Hz), 3.33 (s, 2H), 2.72 (t, 2H, J=5.6 Hz), 2.49 (t, 2H, J=5.9 Hz), 2.26 (s, 3H), 1.73–1.83 (m, 2H); $^{13}$C NMR (100 MHz, DMSO-d$_6$): 29.0, 32.2, 45.8, 52.3, 56.9, 57.3, 64.4, 112.3, 113.5, 126.8, 127.0, 134.8, 156.8.

EXAMPLE 91

6-(6-methanesulfonylthiohexyloxy)-2-methyl-1,2,3,4-tetrahydroisoquinoline

MS: 356 (100, M$^+$–1), 278 (24), 162 (33), 146 (11), 120 (39); $^1$H NMR (500 MHz, CDCl$_3$): 6.93 (d, 1H, J=8.4 Hz), 6.69 (d+d, 1H, J=2.6 Hz, J=8.4 Hz), 6.63 (d, 1H, J=2.5 Hz), 3.92 (t, 2H, J=6.3 Hz), 3.59 (s, 2H), 3.32 (s, 3H), 3.18 (t, 2H, J=7.4 Hz), 2.92 (t, 2H, J=6.1 Hz), 2.74 (t, 2H, J=6.1 Hz), 2.50 (s, 3H), 1.76–1.82 (m, 4H), 1.49–1.51 (m, 4H); $^{13}$C NMR (120 MHz, CDCl$_3$): 25.5, 28.3, 29.0, 29.1, 29.5, 36.4, 45.7, 50.6, 52.6, 57.1, 67.6, 112.7, 113.9, 126.2, 127.4, 134.6, 157.5.

EXAMPLE 92

6-(5-methanesulfonylthiopentyloxy)-2-methyl-1,2,3,4-tetrahydroisoquinoline

MS: 342 (100, M$^+$–1), 264 (36), 162 (68), 146 (18), 120 (68); $^1$H NMR (400 MHz, CDCl$_3$): 6.93 (d, 1H, J=8.6 Hz), 6.68 (d+d, 1H, J=2.7 Hz, J=8.6 Hz), 6.63 (d, 1H, J=2.2 Hz), 3.94 (t, 2H, J=6.3 Hz), 3.60 (s, 2H), 3.32 (s, 3H), 3.20 (t, 2H, J=7.3 Hz), 2.93 (t, 2H, J=6.1 Hz), 2.75 (t, 2H, J=6.1 Hz), 2.51 (s, 3H), 1.77–1.87 (m, 4H), 1.59–1.64 (m, 2H); $^{13}$C NMR (120 MHz, CDCl$_3$): 25.2, 28.6, 29.1, 29.3, 36.3, 45.7, 50.7, 52.7, 57.2, 67.4, 112.7, 113.9, 126.2, 127.4, 134.6, 157.4.

EXAMPLE 93

6-(4-methanesulfonylthiobutoxy)-2-methyl-1,2,3,4-tetrahydroisoquinoline

MS: 328 (100, M$^+$–1), 250 (21), 162 (62), 146 (12), 120 (38); $^{13}$C NMR (100 MHz, CDCl$_3$): 26.5, 28.0, 29.0, 36.2, 45.7, 50.8, 52.6, 57.1, 66.9, 112.7, 113.9, 126.4, 127.4, 134.3, 157.1.

EXAMPLE 94

6-(3-methanesulfonylthiopropoxy)-2-methyl-1,2,3,4-tetrahydroisoquinoline

MS: 314 (100, M$^+$–1), 162 (39), 146 (19), 120 (24); $^1$H NMR (500 MHz, CDCl$_3$): 6.93 (d, 1H, J=8.4 Hz), 6.68 (dd, 1H, J=2.6 Hz, J=8.3 Hz), 6.64 (d, 1H, J=2.6 Hz), 4.05 (t, 2H, J=7.4 Hz), 3.57 (s, 2H), 3.37 (t, 2H, J=7.1 Hz), 3.32 (s, 3H), 2.93 (t, 2H, J=6.0 Hz), 2.72 (t, 2H, J=6.0 Hz), 2.48 (s, 3H), 2.46 (m, 2H); $^{13}$C NMR (125 MHz, CDCl$_3$): 29.2, 29.4, 33.2, 45.8, 50.4, 52.6, 57.2, 65.3, 112.6, 113.9, 126.9, 127.5, 134.9, 156.9.

Test method

The affinity of the test compounds on the α$_2$-adrenoceptor was established using the recombinant mammalian S115 cell line expressing the human α$_{2A}$(α$_2$-C10)-adrenoceptor (7) in a radioligand receptor binding assay. The cells were harvested and suspended in 30 v/w of 50 mM Tris with 5 mM EDTA (pH 7.5 at 4° C.) and homogenized in Teflon-glass homogenizer. Cell homogenate was then centrifuged twice at 47,800×g (Sorvall RC-5C) for 30 min at 4° C. with re-suspension by two strokes in Tris/EDTA buffer. The final pellet was re-suspended in ten v/w of incubation buffer (50 mM KH$_2$PO$_4$ buffer, pH 7.5 at 25° C.) and distributed in aliquots to be stored at −80° C. for later use.

In a competition binding experiment, the radioligands were incubated at 1 nM [$^3$H]-rauwolscine with the cell suspension (20–50 μg of total protein per tube) with or without presence of a test compound in 50 mM KH$_2$PO4 (pH 7.5 at 25° C.) in a total volume of 0.25 ml. Non-specific binding of the radioligand was determined using 0.1 mM oxymetazoline. After a 30 min incubation at 25° C., incubation was terminated by rapid filtration through GF/B filters using a cell harvester. Inhibition experiments were analysed using a non-linear regression curve-fitting computer program to obtain K$_i$ values.

The results are shown in Table 2 below.

TABLE 2

| Alpha-2-receptor active compounds of formula (VI) | | | | | |
|---|---|---|---|---|---|
| compound | R$_1$ | R$_2$ | R$_3$ | R$_4$ | α$_{2A}$aff/ nM |
| 5b | O(CH$_2$)$_5$CN | H | H | Me | 1040 |
| 5c | H | O(CH$_2$)$_5$CN | H | Me | 3710 |
| 5d | 3,4-difluoro-rophenyl-methoxy | H | H | Me | 318 |
| 5e | H | 3,4-difluoro-rophenyl- | | | 1431 |

TABLE 2-continued

Alpha-2-receptor active compounds of formula (VI)

| compound | $R_1$ | $R_2$ | $R_3$ | $R_4$ | $\alpha_{2A}$aff/ nM |
|---|---|---|---|---|---|
| 5f | H | methoxy H | 3,4-difluo- rophenyl- methoxy | Me | 490 |
| 5g | BuO | H | H | Pr | 264 |
| 5h | Cyclohexyl- methoxy | H | H | Me | 750 |
| 5i | H | Cyclohexyl- methoxy | H | Me | 977 |
| 5j | H | H | Cyclohexyl- methoxy | Me | 173 |
| 5k | $CH_3(CH_2)_{13}O$ | H | H | Me | 6485 |
| 5l | H | $CH_3(CH_2)_{13}O$ | H | Me | 266 |
| 5m | H | H | $CH_3(CH_2)_{13}O$ | Me | 25000 |

For the purpose of the invention, the alpha-2-receptor compound or its pharmaceutically acceptable salt can be administered by various routes. The suitable administration forms include, for example, oral formulations; parenteral injections including intravenous, intramuscular, intradermal and subcutanous injections; transdermal or rectal administration forms.

The required dosage of the compounds will vary with the particular condition being treated, the severity of the condition, the duration of the treatment, the administration route and the specific compound being employed. A typical therapeutically effective daily dose can, for example, vary from 0.1 µg to 10 mg per kilogram body weight of an adult person.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

We claim:

1. A process of preparing a tertiary amine compound of the formula (V)

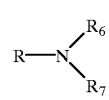

(V)

where R is alkyl and $R^6$ and $R^7$ are alkyl groups which are optionally substituted or where $R^6$ and $R^7$ form a ring or ring system, wherein said method comprises the steps of
  a) reacting a compound of the formula (I)

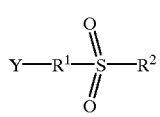

(I)

wherein Y is a solid or soluble support, where Y may include a residue of a functional group having been attached to said support, said functional group having been hydroxy, amino, thio, epoxy or halogen,
$R^1$ is aryl, heteroaryl, alkyl chain or a ring or ring system, which may include a heteroatom, or $R^1$ is nothing, and $R^2$ is vinyl;

$CH_2CH_2X$, where X is halogen; or $R^3C$═$CHR^4$ or $R^3CH$—$CH_2R^4X$, where $R^3$ and $R^4$ are the same or different and are alkyl, acyl, carbonyl, cyano or nitro groups and X is halogen, with a secondary amine (II)

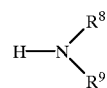

(II)

wherein $R^8$ and $R^9$ are the same as or different from the groups $R^6$ and $R^7$ defined above and are alkyl groups, which are optionally substituted, or form a ring or ring system, to give a compound (III)

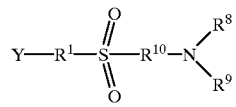

(III)

wherein $R^{10}$ is $CH_2CH_2$ or $R^3CH$—$CHR^4$, where $R^3$ and $R^4$ are as defined above, b) quaternising the compound (III) with an alkyl halide RX where R is alkyl and X is halide or an ester of an alkyl sulfonic acid, to give a quaternary ammonium ion (IV)

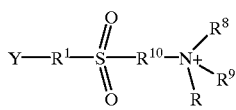

(IV)

c) cleaving the quaternary ammonium ion (IV) to give the tertiary amine (V), and, in case $R^8$ and $R^9$ are different from $R^6$ and $R^7$, carrying out the reactions interchanging these groups as separate steps between steps a) and b) above.

2. The method according to claim 1, wherein the secondary amine (II) is a tetrahydroisoquinoline of the formula (IIa)

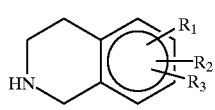

(IIa)

wherein $R_1$, $R_2$ and $R_3$ are the same or different and which are H, alkyl or an ether group.

3. The method according to claim 2, wherein $R_1$ is an ether group —OR' and R' is a protection group, wherein the the compound (III) obtained in said step a) has the formula (IIIa)

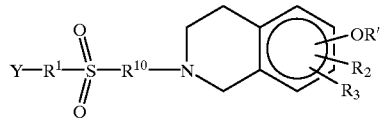

(IIIa)

whereafter said protection group OR' is removed to give the the corresponding OH-substituted compound (IIIb)

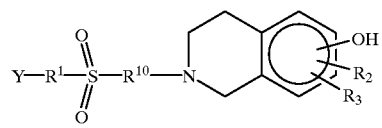

(IIIb)

after which the compound (IIIb) is subjected to Mitsunobu ether formation with R"OH to give the compound (IIIc)

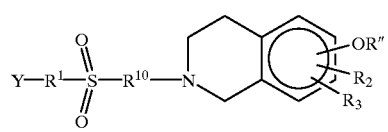

(IIIc)

after which compound (IIIc) is subjected to said steps b) and c) to release the desired tertiary amine (Va)

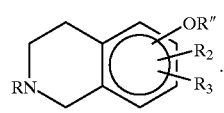

(Va)

4. The method according to claim 1 wherein $R^1$ is $CH_2CH_2$ or nothing.

5. The method according to claim 1 wherein the compound of formula (I) is

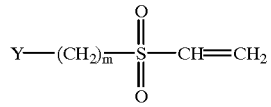

wherein m is 0 or 2 and Y has the formula Supp-O or Supp-NH and Supp is the support optionally including a tethering group, to which the functional hydroxy or amino group has been attached.

6. The method according to claim 3 wherein said protection group is removed by methanolyse.

7. The method according to claim 5 wherein the tethering group is methylene.

* * * * *